United States Patent
Watzele et al.

(10) Patent No.: US 7,156,996 B2
(45) Date of Patent: Jan. 2, 2007

(54) MULTICHAMBER MICRODIALYSIS DEVICE

(75) Inventors: Manfred Watzele, Wellheim (DE); Bernd Buchberger, Peissenberg (DE); Hans Schels, Munich (DE); Horst Menzler, Seeshaupt (DE); Ulrike Fischer, Penzberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 327 days.

(21) Appl. No.: 10/652,938

(22) Filed: Sep. 2, 2003

(65) Prior Publication Data

US 2004/0195163 A1 Oct. 7, 2004

(30) Foreign Application Priority Data

Apr. 7, 2003 (DE) .......................... 203 05 570 U

(51) Int. Cl.
*B01D 63/00* (2006.01)
*C12M 1/12* (2006.01)
*B01L 11/00* (2006.01)

(52) U.S. Cl. .................... 210/321.71; 210/321.75; 210/321.72; 422/101; 422/102; 435/297.1; 435/297.2; 435/297.5

(58) Field of Classification Search .................. None
See application file for complete search history.

(56) References Cited

U.S. PATENT DOCUMENTS 5,047,215 A * 9/1991 Manns ..................... 422/101
5,462,874 A * 10/1995 Wolf et al. ............... 435/297.5
5,783,075 A 7/1998 Eddleman et al. .......... 210/232
6,039,871 A 3/2000 Sykaluk ................. 210/321.71
6,458,275 B1 10/2002 Shukla et al. ............ 210/321.6
6,670,173 B1 * 12/2003 Schels et al. ............ 435/297.2

FOREIGN PATENT DOCUMENTS

DE   G9105550.4   9/1991
EP   0596482 B1   5/1994
WO   WO 00/44877  8/2000

* cited by examiner

*Primary Examiner*—Krishnan S. Menon
(74) *Attorney, Agent, or Firm*—Marilyn L. Amick; Roche Diagnostics Operations, Inc.

(57) ABSTRACT

The invention is a multichamber microdialysis device with a multitude of sample chambers in close side by side arrangement (similar to a microtiter plate) for receiving liquid samples, and at least one dialysate chamber for receiving a dialysate liquid. The sample chambers are surrounded by circumferential sidewalls and are in liquid exchange contact to a neighboring dialysis chamber via an exchange opening covered by a semipermeable membrane. The semipermeable membrane is fixed liquid-tight to the walls of the sample chamber, so that a diffusion exchange between the sample chamber and the correspondingly neighboring dialysate chamber is only possible via the membrane. Consequently, only molecules with a molecular weight below the molecular cut-off of the semipermeable membrane can diffuse from the sample chamber to the dialysate chamber or from the dialysate chamber to the sample chamber.

15 Claims, 3 Drawing Sheets

MULTICHAMBER MICRODIALYSIS DEVICE

The invention is concerned with a multichamber microdialysis device with a multitude of sample chambers in close side by side arrangement (similar to a microtiter plate) for receiving liquid samples, and at least one dialysate chamber for receiving a dialysate liquid. The sample chambers are each surrounded by circumferential sidewalls and are in liquid exchange contact to a neighboring dialysis chamber via an exchange opening covered by a semipermeable membrane. The semipermeable membrane is fixed liquid-tight to the walls of the sample chamber, in such a manner that a diffusion exchange between the sample chamber and the correspondingly neighboring dialysate chamber is only possible via the membrane; consequently, only molecules with a molecular weight below the molecular cut-off of the semipermeable membrane can diffuse from the sample chamber to the dialysate chamber or from the dialysate chamber to the sample chamber.

In order to minimize the required sample quantity, the multichamber microdialysis devices this invention relates to, are as small as possible. Formats corresponding to the commonly available microtiter plates with 96 chambers (also designated microwell or multiwell plates) are particularly preferred, so that automatic dosing equipment and other devices adjusted to the microtiter plate formats, can be used. For this, the distance between the centers of the chambers is 9 mm.

In the multipurpose microdialysis devices to which the invention refers the exchange surface of the membrane available for the diffusion exchange (in the exchange opening between sample chamber and dialysate chamber) is typically smaller than 100 $mm^2$. The invention preferably is used in devices wherein the effective membrane surface is smaller than 50 $mm^2$. Generally, the sample chamber volume is below 200 $mm^3$; in preferred cases of application of the invention it is even below 100 $mm^3$.

Such multichamber microdialysis devices are used for several analytic and preparative purposes in chemical and biochemical laboratories. In the language commonly used in laboratories, they are also denominated "Multiwell Dialyzers".

An important area of application is the equilibrium dialysis, in particular in protein bonding tests. Here, multichamber microdialysis devices are used which have a separated dialysate chamber assigned to each sample chamber (1:1 arrangement). Into one of the chambers, respectively, samples of substances are introduced, the bonding capacity of which is to be tested with a protein contained in the neighboring chamber. The molecular cut-off of the membrane is chosen such that the protein is not able to diffuse through it, whereas a diffusion exchange of the smaller molecule of the substance to be investigated is possible through the semipermeable membrane. If the test substance bonds with the protein, an enrichment of the test substance in the chamber containing the protein will take place. This enrichment can be detected, for example, with a radioactive marking of the test substance. If no enrichment can be observed, it can be concluded that the test substance does not bond the protein. Such tests are of particular importance for the screening of a large number of test substances with respect to their potential pharmaceutical activity.

Another field of application is the equilibration of samples from biological liquids. To this end, the samples portioned in sample chambers exchange with a common neighboring dialysate chamber via the semipermeable membrane (N:1 arrangement), containing a buffer solution. An equilibration of the samples originating from different biologic environments, which is a precondition for the comparability of subsequently performed tests, is performed by diffusion exchange.

A further application example are tissue cultures or the cell-free biochemical synthesis of proteins or other polypeptides. Here, the sample chambers contain the tissue sample or the high-molecular components necessary for the cell-free biosynthesis, respectively, whereas a supply liquid with relatively low-molecular nutriments required for the biosynthesis is contained in the neighboring dialysate chamber.

These examples show that the terms "dialysate liquid" and "dialysate chamber", in the scope of the invention, must not be understood in a limited way. In particular it must not be understood that the diffusion of the low molecular components essentially takes place from the sample chamber toward the dialysate chamber. The invention is rather targeted to multichamber microdialysis devices for most different cases of application, wherein any kind of diffusion exchange takes place via a semipermeable membrane between two chambers which are in fluid communication only via the exchange surface, i.e. through the semipermeable membrane.

A special problem within the development of such multiwell dialyzers is the fastening of the membrane at the marginal area of the exchange opening of the sample chambers. On one hand, it must fulfil high requirements. In particular, a reliable sealing between the membrane and the circumferential sidewall of the sample chambers must be obtained, because each leakiness enables the diffusion of molecules with a molecular weight above the molecular cut-off of the semipermeable membrane, thus leading to errors. On the other hand, the fastening of the membrane to the chamber wall is subject to restrictions which result from the limited space available in a multiwell dialyzer which has a plurality of small sample chambers arranged very close to each other on a single level; this leads to substantial design restrictions. In spite of these technical problems, the fastening of the membrane to the cell wall must be as cost-effective as possible, as multiwell dialyzers generally are used only once (disposable) and are required in large quantities.

A multiwell dialyzer for equilibrium dialysis is described in EP 0596482 B1. There, it is pointed out that the reliable separation of the sample side of the membrane from the opposite side (i.e. the dialysate side) is a difficult problem. In particular, it is pointed out that dialysis membranes are made of cellulose acetate or of regenerated cellulose, and it is a known fact that it is difficult to fix these membranes by means of thermal techniques or by means of adhesives in a reliable and tight way. It says that it was common to close the sample area by using a hose-shaped membrane, closing it with a knot or by means of a clip. Furthermore, a device known from DE-U-9105550 is referred to, wherein a membrane is mounted between rigid plates, with cavities arranged in these plates, and wherein an O-ring is used in order to ensure the required tightness. However, such an O-ring sealing is considered insufficient.

In order to solve these problems EP 0596482 suggests a design wherein a single membrane is used for a plurality of sample chambers. Here, the tightness is to be obtained by pressing a perforated template against the membrane which is situated above the exchange openings of the sample chambers, thus pulling it over the outer walls of the sample chambers. However, reliable sealing cannot be achieved in this manner, in particular, because the material of dialysis membranes is of insufficient elasticity.

U.S. Pat. No. 6,458,275 also refers to laboratory devices for equilibrium dialysis. It is stated that the devices so far available for this purpose have only one single chamber, allowing the processing of only one sample each. However, for many applications screening techniques with a high throughput were required, wherein it was necessary to process a high amount of samples in a short time. For this purpose, a multiwell dialyzer with at least 96 chambers and a special design of a closing part at the input opening of the chambers, is proposed. With respect to the mounting of the membrane, only the general statement is made that each physical or chemical method is appropriate. A solution of the problems described above is not proposed.

Basing upon these facts, the invention aims to create a multiwell dialyzer which is simple and inexpensive, and which at the same time works reliably, in particular with respect to the tightness of the membrane at the circumference of the exchange opening of the sample chambers.

The object is achieved by a multiwell dialyzer according to claim 1.

In general technology it is not uncommon to fix flat constructive parts, e.g. membranes, by clamping them between two constructive parts. In biotechnology, this basic principle has already been used, too. In WO 00/44877, a bioreactor for the cell-free biosynthesis of proteins is described, wherein a dialysis membrane is clamped in a tight way between two so-called chamber parts. There, too, the membrane is pressed, by a projecting rib, into a groove aligned with that rib. However, the constructive and manufacturing conditions of the bioreaction module described in WO 00/44877 differ fundamentally from a multiwell dialyzer:

In a multiwell dialyzer a plurality of sample chambers are arranged close to each other (with exchange chambers openings on a common level) on a restricted space (overall surface preferably smaller than 120 $cm^2$), whereas only a single "system chamber" is required in the bioreaction module.

The dimensions are on a different scale. The bioreactor represented in WO 00/44877 has an inner diameter of approximately 20 mm and a resulting effective membrane surface of more than 300 $mm^2$. The dimensions of the constructive parts between which the membrane is clamped, are correspondingly larger. In a multiwell dialyzer, however, the sample chamber dimensions are so small that the exchange surface of the membranes typically is only about 20 $mm^2$.

Due to the relatively large dimensions, in WO 00/44877 it is possible to make the two chamber parts, between which the membrane is clamped, mechanically strong and with a relatively large wall thickness. Compared to this, the restricted space in a multiwell dialyzer causes a very small wall thickness of the constructive parts, and thus in substantial strength problems.

In a single module, the mounting of the membrane is no particular problem. Due to its large dimensions, it can be centered and mounted, as described in WO 00/44877, by cast-integrated pins fitting into corresponding holes in the membrane (aligned to the pins). Due to the space restrictions in a multiwell dialyzer, a corresponding design is not possible there.

In the earlier known design, the sealing is essentially based on the fact that the membrane is tensioned by the pins; thus, the sealing rib presses against a tensioned membrane. In case of a multiwell dialyzer, the possible overall width of the sealing area is limited by the face width of the side wall (thus, by the thickness of the side wall which is typically only about 0.8 mm). These spatial restrictions do not allow the use of centering or mounting pins.

The thickness of the dialysis membrane results from its dialysis properties and depends on its surface dimensions. Thus, the very different surface dimensions lead to completely different mechanical circumstances in a multiwell dialyzer, for example with respect to the bending stresses existing at the peripheral marginal section of the membrane, as compared to a much bigger single module, as described in WO 00/44877.

The invention is hereafter described in more detail with reference to the exemplary embodiments shown in the figures. The described characteristics can be used individually or in combination to create preferred embodiments of the invention. In the figures.

Figure 1:
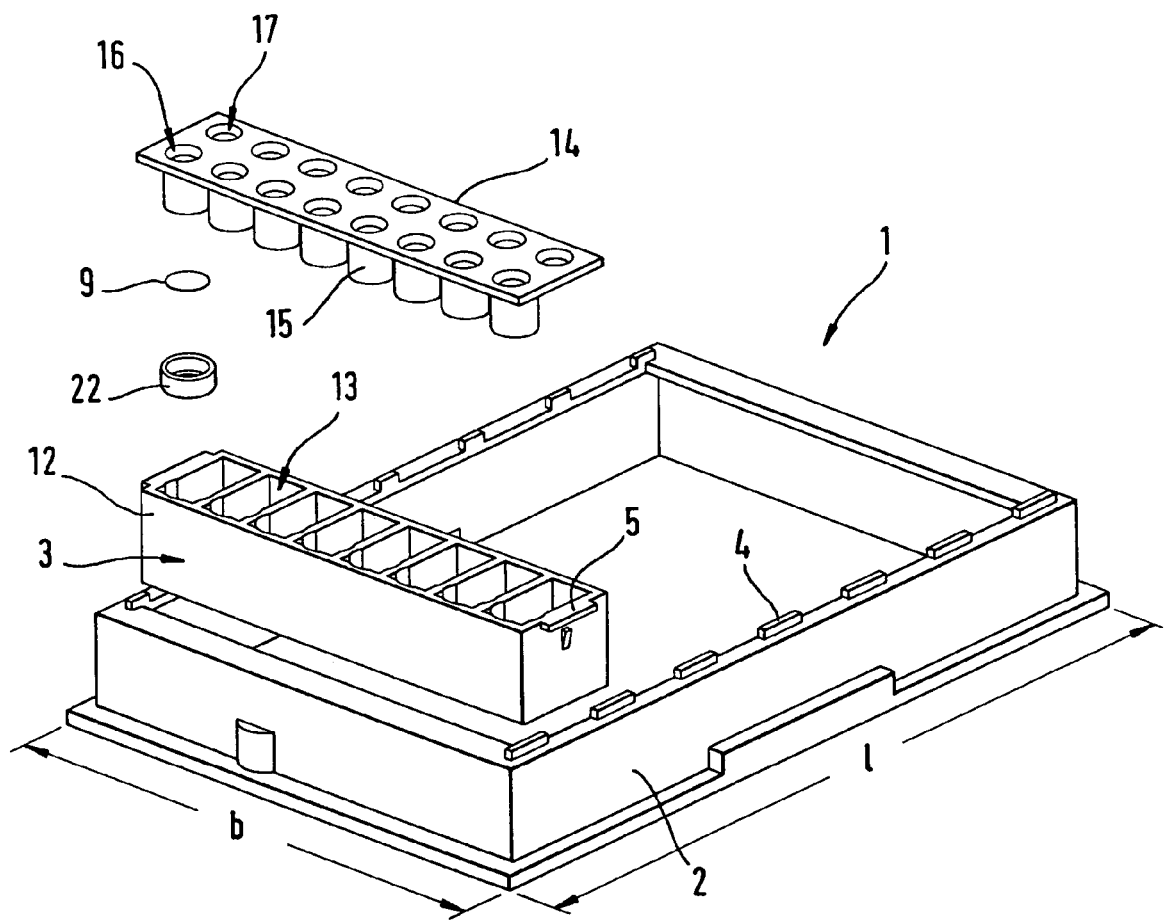
FIG. 1 shows a perspective view of a multiwell dialyzer according to the invention.
Figure 2:
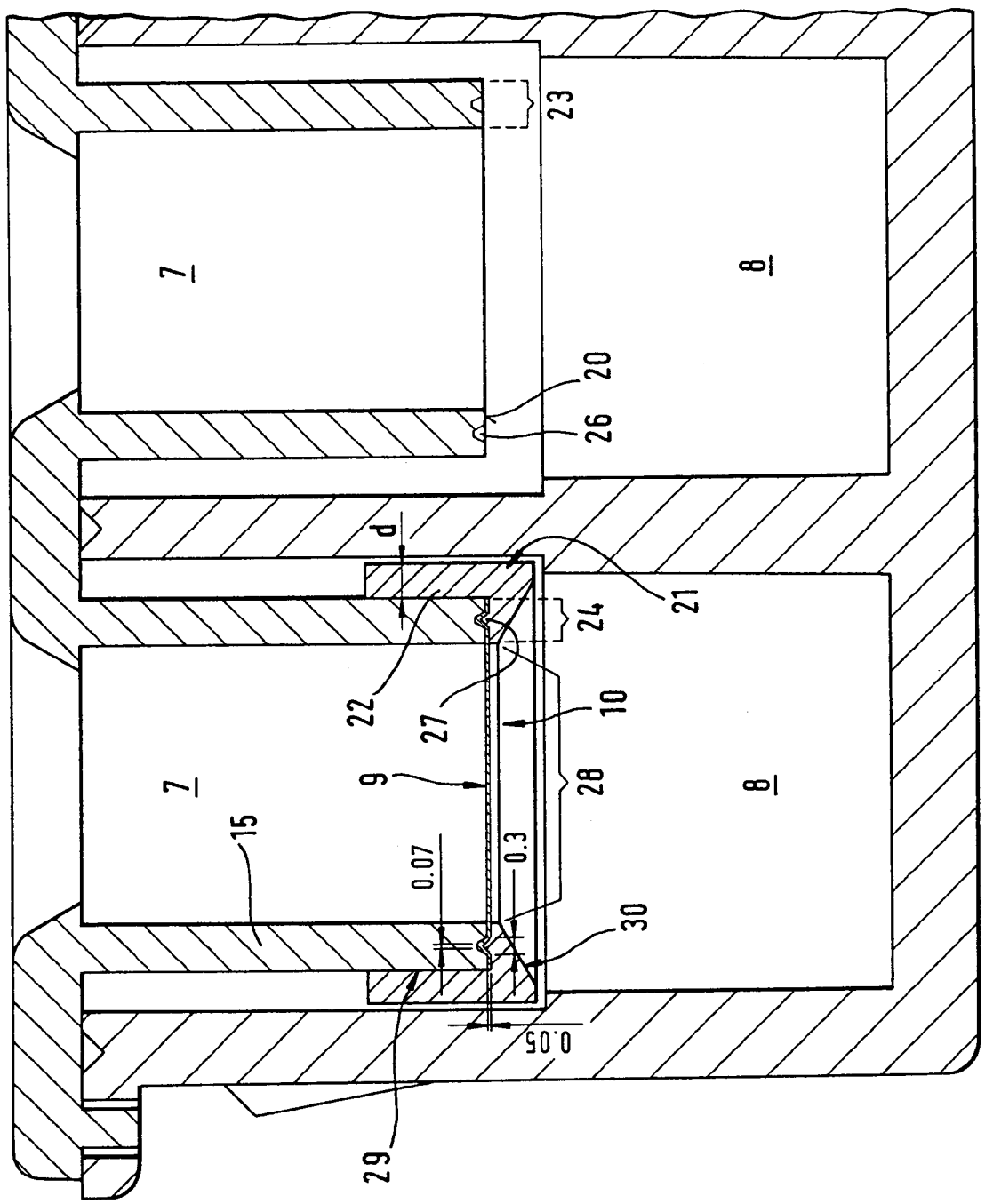
FIG. 2 shows a section through a module of the multiwell dialyzer of FIG. I.

The multiwell dialyzer shown in FIGS. 1 and 2 has a modular structure. It consists of a frame 2 and a plurality of chamber modules 3, which can be inserted in an exactly defined position into the frame 2. In the embodiment shown, the positioning is obtained by means of positioning shoulders 4,5 matching each other, of the frame 2 and the module 3.

The modules 3 include eight sample chambers 7 and eight dialysate chambers 8, which are pairwise in fluid exchange contact to each other through an exchange opening 10 covered by a semipermeable membrane 9. In the embodiment shown, each module 3 consists of a trough part 12 with eight individual troughs 13, and of a chamber part 14 with eight cylindrical circumferential sidewalls 15, each protruding into one trough 13.

The sample chambers 7 enclosed by sidewalls 15 and membranes 9 are accessible from the upper side via a sample opening 16. In pairwise arrangement with each sample opening 16, there is a dialysate opening 17. It provides access from the upper side to a respective dialysate chamber enclosed by an individual trough 13 and the membrane 9. The sample chambers 7 and the dialysate chambers 8 are separated from each other. They are only in contact to a neighboring dialysate or sample chamber via one exchange opening 10 each (1:1 arrangement).

The multiwell dialyzer 1 exactly corresponds to the dimensions of common microtiter plates. Six modules 3 with 16 openings each (eight sample openings 16 and eight dialysate openings 17) can be positioned into the frame 2. This results in a total of 96 openings arranged with a center distance of 9 mm, respectively. Thereby, samples and other liquids can be conveniently dosed into the openings 16,17, using common laboratory devices.

It is important for the proper function of the multiwell dialyzer 1 that the semipermeable membranes 9 are fixed liquid-tight to the circumferential walls 15 of the sample chambers 7, in such a manner that a diffusion exchange between a sample chamber 7 and the neighboring dialysate chamber is only possible for molecules the molecular weight of which is below the molecular cut-off of the membrane. This sealing fixation can be obtained by clamping a circumferential peripheral marginal section stripe of the membrane 9 between the face 20 of the circumferential side wall 15 and a fixing part 21. In the shown embodiment, the fixing part 21 is shaped as a fixing ring 22. The regions where the face 20 of the side wall 15 and the fixing part 21 are in contact to the membrane 9, are also designated as mounting regions 23 and 24, respectively.

The mounting region 23 of the face 20 comprises a circumferential groove 26, and the mounting region 24 of the fixing part 21 comprises a protruding rib fitting into the groove 26. This rib presses the membrane at the peripheral marginal section clamped between the mounting regions 23,24 into the groove 26. The dimensions indicated in FIG. 2, given in millimeters, show that the size is very small. In spite of the narrow groove width (for example, 0.3 mm) and a correspondingly small height of the protruding rib 27 (for example, 0.15 mm), an excellent long-term sealing is achieved.

It is advantageous for the sealing effect if the limiting edges of the groove 26 and the front edge of the protruding rib 27 are as smooth and sharp-edged as possible. Die-cast plastic parts made with die tools wherein the corresponding shape surfaces were polished, have proven suitable.

Due to the spatial conditions in a multiwell dialyzer the wall thickness d of the fixing rings 22 at the level of the membrane 9, measured in radial direction, is very small. Preferably, it is at most 1.5 mm, particularly preferred it is at most 1 mm. The practical evaluation of the invention has shown that it is sufficient, in spite of these small dimensions, if the fixing rings 22 are fixed to the circumferential side walls 15 of the sample chambers 7 by frictional connection only (e.g. by a press fit 29). In order to obtain an even pressure onto the membrane 9, the machine parts used for pressing together the rings and the chamber parts 14 (with the side walls 15) during production, are preferably spring-loaded.

The effective surface (the surface not clamped between the mounting regions 23,24) of the membrane 9 is designated exchange surface 28. According to a preferred embodiment, the limiting surface 30 of the fixing parts 21 which is adjacent to the exchange surface 28, has a conical shape, at least partially, so that the diameter of the exchange opening 10 increases towards the dialysate chamber 8. By this design feature the contradictory requirements which the fixing part 21 has to fulfil with respect to the necessary strength on one hand and with respect to the necessary dialysis exchange on the other hand, are met in an optimal way.

In spite of the very small dimensions of the components of the multiwell dialyzers according to the invention, an economic production is possible, e.g. with a method in which eight membranes are punched out for a module 3, pushed into eight corresponding depressions of a production tool, and transferred from there into eight correspondingly positioned fixing rings (positioned with the protruding rib 27 in upward direction). After that, the step of pressing with the chamber parts 14 is performed, wherein a defined pressure force is ensured by means of spring-loaded pressing tools. The connection of the chamber parts 14 and the trough parts 12 is preferably performed by ultrasonic welding. The ultrasonic effect can simultaneously improve the cohesion of the rings 22 to the walls 15.

Figure 3:
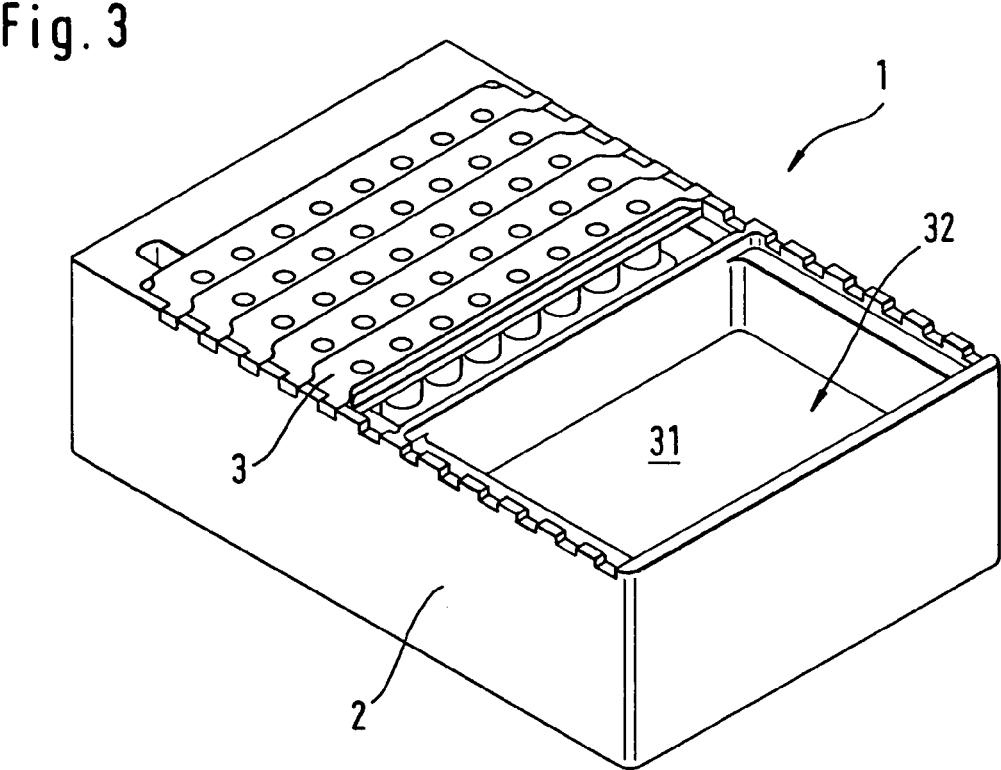
FIG. 3 shows a perspective image of a second embodiment of a multiwell dialyzer according to the invention.
Figure 4:
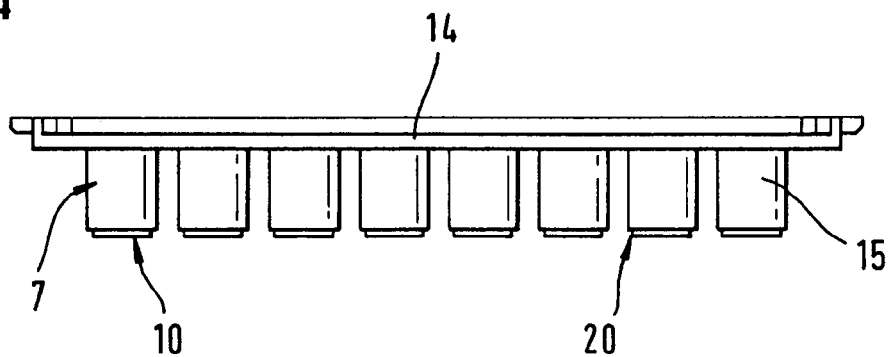
FIG. 4 shows a lateral view of a chamber part of the multiwell dialyzers of FIG. 3.
Figure 5:
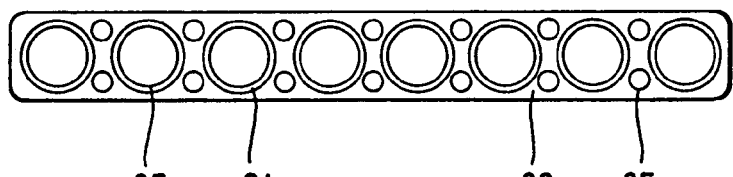
FIG. 5 shows a top view onto an associated support piece.

The embodiment shown in FIGS. 3 to 5 differs from the FIGS. 1 and 2 essentially by the fact that a plurality of sample chambers 7 (inside the cylindrical walls 15 of the shown chamber parts 14) are in contact to a common dialysate chamber 31. The multiwell dialyzer 1 includes two dialysate chambers 31, surrounded by corresponding troughs 32 of the frame 2, respectively. The sample chambers 7 protrude into the troughs 32 in such a manner that they are in contact, via exchange openings 10 covered by membranes (not shown), to a dialysate located in the dialysate chamber 31. Another particularity is the fact that the sample chambers 7 of a module 3 are fixed to the faces 20 of the walls 15 by means of a common fixing part 32. The fixing part 33 includes a plurality of ring profiles 34, each having a protruding rib 27 fitting into a corresponding groove, in the same way as the fixing rings 22 in FIG. 2. The connection of the common fixing part 33 with the corresponding chamber part 33 can be performed with usual plastics technology methods, e.g. via plastic columns (not shown) fitting into corresponding bores 35 of the common fixing part 33.

The invention claimed is:

1. A multichamber microdialysis device comprising
a plurality of sample chambers in close side by side arrangement, said sample chambers being defined by circumferential side walls having a first open end for taking up liquid samples into the sample chamber and a second open end providing an exchange opening, and
a dialysate chamber for taking up a dialysate liquid,
wherein the exchange opening of each sample chamber is covered with a separate semipermeable membrane fixed liquid-tight to the circumferential side walls of the sample chamber in such a manner to provide a diffusion exchange between the sample chamber and the dialysate chamber when the second end of the sample chamber is placed in contact with the dialysate liquid, and
wherein a peripheral marginal section of each semipermeable membrane is clamped between a front face of the circumferential side wall of the sample chamber and a fixing part, wherein each fixing part comprises a ring-shaped portion presenting a circumferential mounting region and an annular wall extending from the perimeter of the ring-shaped portion, the diameter of said annular wall selected to allow frictional engagement of the annular wall with the circumferential side walls of the sample chambers, wherein the outer diameter of a region where the annular wall frictionally engages the circumferential side walls exceeds the sample chamber diameter by not more than 3 mm, the front face of the side wall consisting of an opposing ring-shaped circumferential mounting region wherein one of the mounting regions consists of a surface and a circumferential groove and the other mounting region consists of a surface and a protruding rib fitting into the groove, by which the membrane is pressed into the groove at its peripheral marginal section and clamped between the ring-shaped circumferential mounting region and the opposing ring-shaped circumferential mounting region.

2. The multichamber microdialysis device of claim 1, wherein each semipermeable membrane has an exchange surface area less than 50 mm$^2$.

3. The multichamber microdialysis device of claim 1, wherein the sample chambers are each in liquid exchange contact with only one of a plurality of dialysate chambers via its exchange opening, and each dialysate chamber is in liquid exchange contact with only one sample chamber.

4. The multichamber microdialysis device of claim 1, wherein the first end of each sample chamber is in contact with a common dialysate chamber via their respective exchange openings.

5. The multichamber microdialysis device of claim 4, wherein the membranes of the sample chambers which are in liquid exchange contact with a common dialysate chamber are fixed by means of a plurality of said fixing parts linked together and spaced to allow the simultaneous attachment of the linked fixing parts to the second end of the sample chambers.

6. The multichamber microdialysis device of claim 1, wherein the semipermeable membrane comprises cellulose acetate or regenerated cellulose.

7. The multichamber microdialysis device of claim 1, wherein the device comprises at least 8 sample chambers.

8. The multichamber microdialysis device of claim 1, wherein the device comprises at least 48 sample chambers.

9. The multichamber microdialysis device of claim 1, wherein the device comprises at least 96 sample chambers.

10. The multichamber microdialysis device of claim 1, wherein the distance between the center of the first open end of each sample chamber to the center of the next adjacent sample chamber is about 9 mm.

11. The device of claim 1 wherein a limiting surface of the fixing part is adjacent to an exchange surface and has at least a partial conical shape whereby the diameter of the exchange opening increases towards the dialysate chamber.

12. The device of claim 1 wherein the dialysate chamber is formed by a trough into which the circumferential side walls protrude.

13. The device of claim 12 wherein the interior surface of the fixing part annular wall is fixed to the outer surface of the circumferential sidewalls of the sample chambers by frictional press fit connection.

14. The multichamber microdialysis device of claim 1 wherein each semipermeable membrane has an exchange surface area of about 20 mm$^2$.

15. A multichamber microdialysis device comprising
a plurality of sample chambers in close side by side arrangement, said sample chambers being defined by circumferential side walls having a first open end for taking up liquid samples into the sample chamber and a second open end providing an exchange opening, and
a dialysate chamber for taking up a dialysate liquid,
wherein the exchange opening of each of the sample chambers is covered with a separate semipermeable membrane fixed liquid-tight to the circumferential side walls of the sample chamber in such a manner to provide a diffusion exchange between the sample chamber and the dialysate chamber when the second end of the sample chamber is placed in contact with the dialysate liquid,
wherein a peripheral marginal section of each semipermeable membrane is clamped between a front face of the circumferential side wall of the sample chamber and a fixing part, wherein each fixing part comprises a ring-shaped portion presenting a circumferential mounting region and an annular wall extending from the perimeter of the ring-shaped portion, and the front face of the side wall consists of an opposing ring-shaped circumferential mounting region, wherein one of the mounting regions consists of a surface and a circumferential groove and the other mounting region consists of a surface and a protruding rib fitting into the groove by which the membrane is pressed into the groove at its peripheral marginal section and clamped between the ring-shaped circumferential mounting region and the opposing ring-shaped circumferential mounting region, and
wherein a surface of the ring-shaped portion of the fixing part facing the dialysate liquid has at least a partial conical shape whereby the diameter of the exchange opening increases towards the dialysate chamber.

* * * * *